United States Patent [19]

Danna et al.

[11] Patent Number: 4,491,865
[45] Date of Patent: Jan. 1, 1985

[54] IMAGE SENSOR ASSEMBLY

[75] Inventors: Dominick Danna, Syracuse; Richard W. Newman, Auburn, both of N.Y.

[73] Assignee: Welch Allyn, Inc., Skaneateles Falls, N.Y.

[21] Appl. No.: 426,927

[22] Filed: Sep. 29, 1982

[51] Int. Cl.³ .................. H04N 7/18; H04N 3/02; H04N 3/14
[52] U.S. Cl. ..................................... 358/98; 358/100; 358/200; 358/213; 358/229; 128/303.15; 128/4
[58] Field of Search .................. 358/98, 100, 200, 213, 358/108, 229; 128/4, 6, 303.15

[56] References Cited

U.S. PATENT DOCUMENTS

| 2,764,149 | 9/1956 | Sheldon . | |
|---|---|---|---|
| 3,832,724 | 8/1974 | Duval | 354/63 |
| 4,028,730 | 6/1977 | Miller | 358/217 |
| 4,074,306 | 2/1978 | Kakinuma et al. | 358/1 |
| 4,253,447 | 3/1981 | Moore et al. | 128/6 |
| 4,344,092 | 8/1982 | Miller | 358/217 |
| 4,413,278 | 11/1983 | Feinbloom | 358/93 |
| 4,441,125 | 4/1984 | Parkinson | 358/213 |
| 4,442,456 | 4/1984 | Iwata et al. | 358/213 |

Primary Examiner—Howard W. Britton
Assistant Examiner—John K. Peng
Attorney, Agent, or Firm—Bruns and Wall

[57] ABSTRACT

A compact image sensor package for use in an endoscope or borescope in which a lens system, a solid state image sensor and a circuit board are mounted in tandem within a cylindrical sealed housing. The assembly is positioned within the viewing head of the instrument so that an image of a given target is recorded on the sensor and an electrical output signal indicative of the image data is transmitted out of the package via either an optical or electrical transmission line.

7 Claims, 5 Drawing Figures

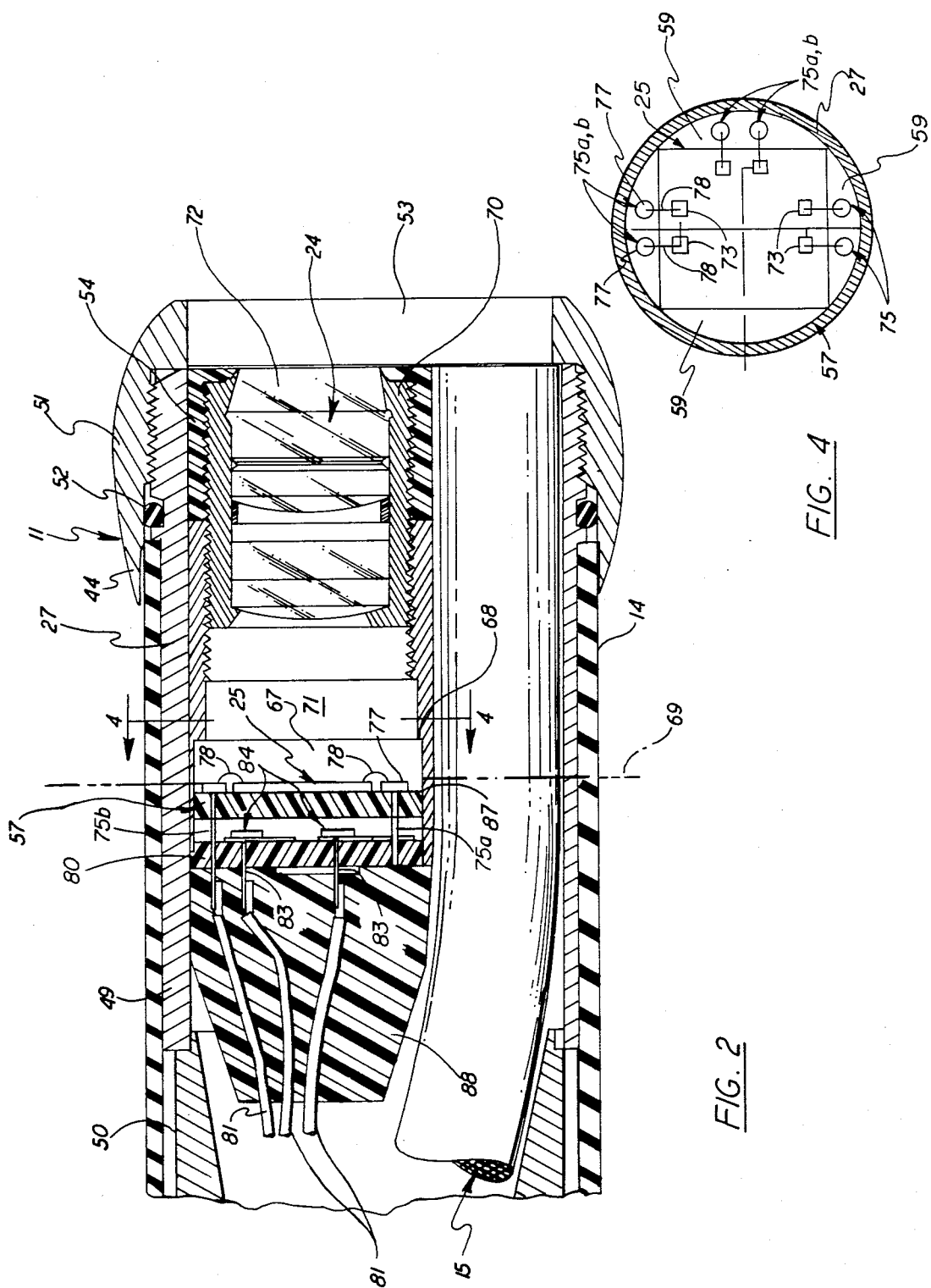

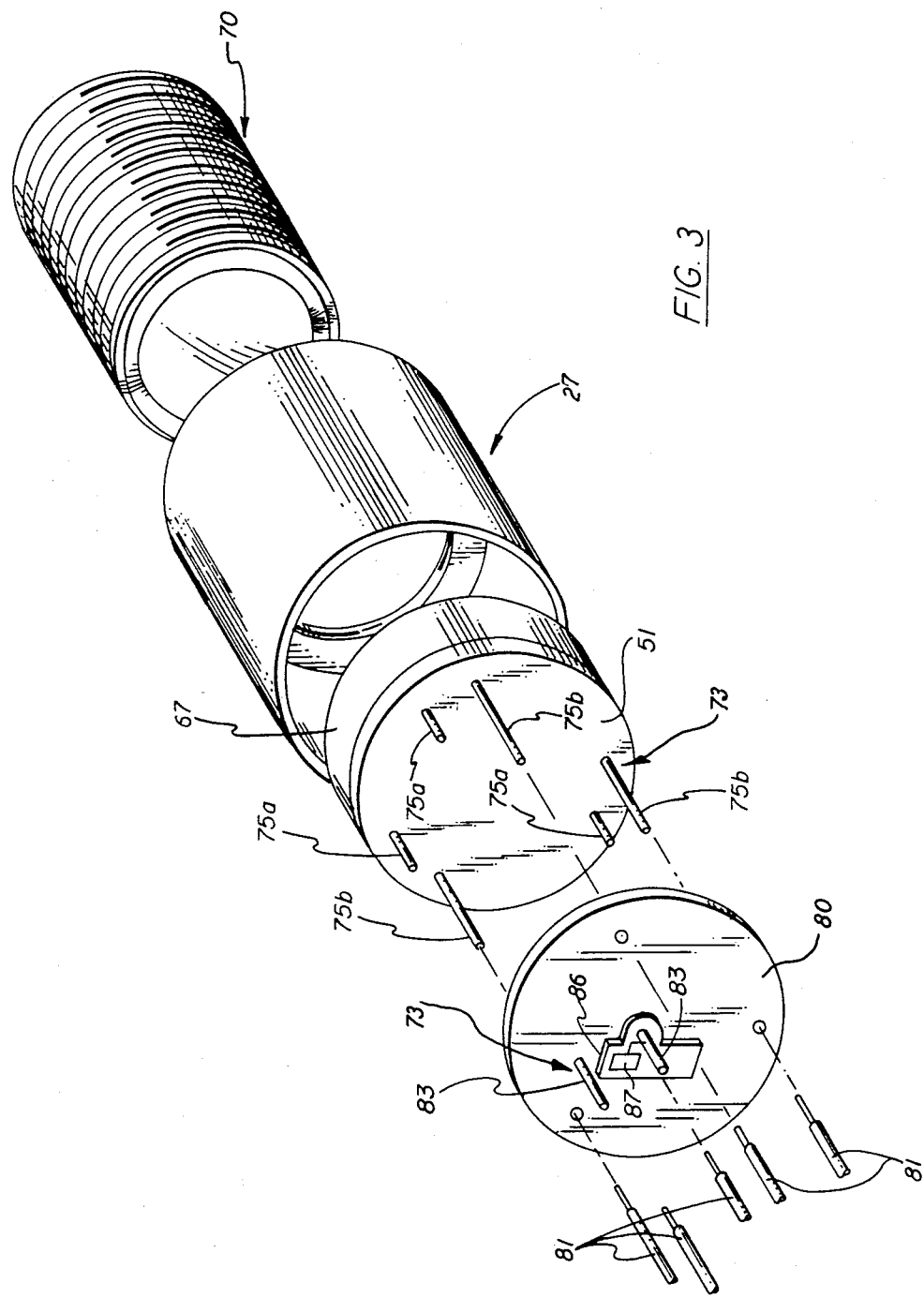

000
IMAGE SENSOR ASSEMBLY

BACKGROUND OF THE INVENTION

This invention relates generally to an endoscope or borescope for providing a full color video image of a generally inaccessible region and, in particular, to a highly compacted imager assembly for use in the viewing head of an endoscope or a borescope.

Sheldon in U.S. Pat. No. 2,764,149 discloses an endoscope for providing a full color video picture of a target situated within a body cavity. The viewing head of the Sheldon device, that is, the section of the instrument which is inserted into the body cavity, contains a rather bulky vidicon tube and a complex three color lighting system which requires that the head be rather large in order to house the various components. Consequently, the Sheldon device can only be used where the receiving cavity is correspondingly large. Kakinuma in U.S. Pat. No. 4,074,306 discloses an improved full color endoscope system in which the light source is taken out of the head and the vidicon tube is replaced by a solid state image sensor. In this new arrangement, the light of three primary colors needed to both illuminate the target and to provide color separation is transmitted into the head via a fiber bundle. Although the Kakinuma device reduces the size and the number of components needed in the viewing head, this advantage may easily be lost through poor packaging.

SUMMARY OF THE INVENTION

It is therefore an object of the present invention to improve endoscopes and/or borescopes.

A further object of the present invention is to compact the optical and electrical components contained in the viewing head of a full color endoscope so that the head may be correspondingly compacted to provide greater access to remote target regions.

A still further object of the present invention is to package the electrical and optical readout components of a color endoscope within a relatively small housing.

Yet another object of the present invention is to provide a small diameter hermetically sealed electro-optical package for providing full color picture information of the target of an endoscope.

These and other objects of the present invention are attained by means of a color endoscope having a viewing head in which is positioned an electro-optical package that includes a hollow housing, a lens system mounted in the front of the housing opening, a solid state image sensor mounted in the housing opening behind the lens system having an image recording surface positioned in the image plane of the lens system, a circuit board also mounted in the housing behind the image sensor having circuitry thereon for processing signals passing to and from the image sensor, and transmission lines passing into and out of the back of the housing for connecting the sensor and the circuit board to a remote electrical section.

BRIEF DESCRIPTION OF THE DRAWINGS

For a better understanding of the present invention as well as further objects and features thereof, reference is had to the following detailed description of the invention which is to be read in conjunction with the accompanying drawings wherein:

FIG. 2 is an enlarged side elevation in section of the viewing head utilized in the endoscope of FIG. 1 showing an electro-optical package contained therein for providing full color video information of a target in the object plane of the lens;

FIG. 3 is an exploded view of the electro-optical package contained in the viewing head shown in FIG. 2;

FIG. 4 is a section taken along lines 4—4 in FIG. 3; and

DESCRIPTION OF THE INVENTION

Figure 1:
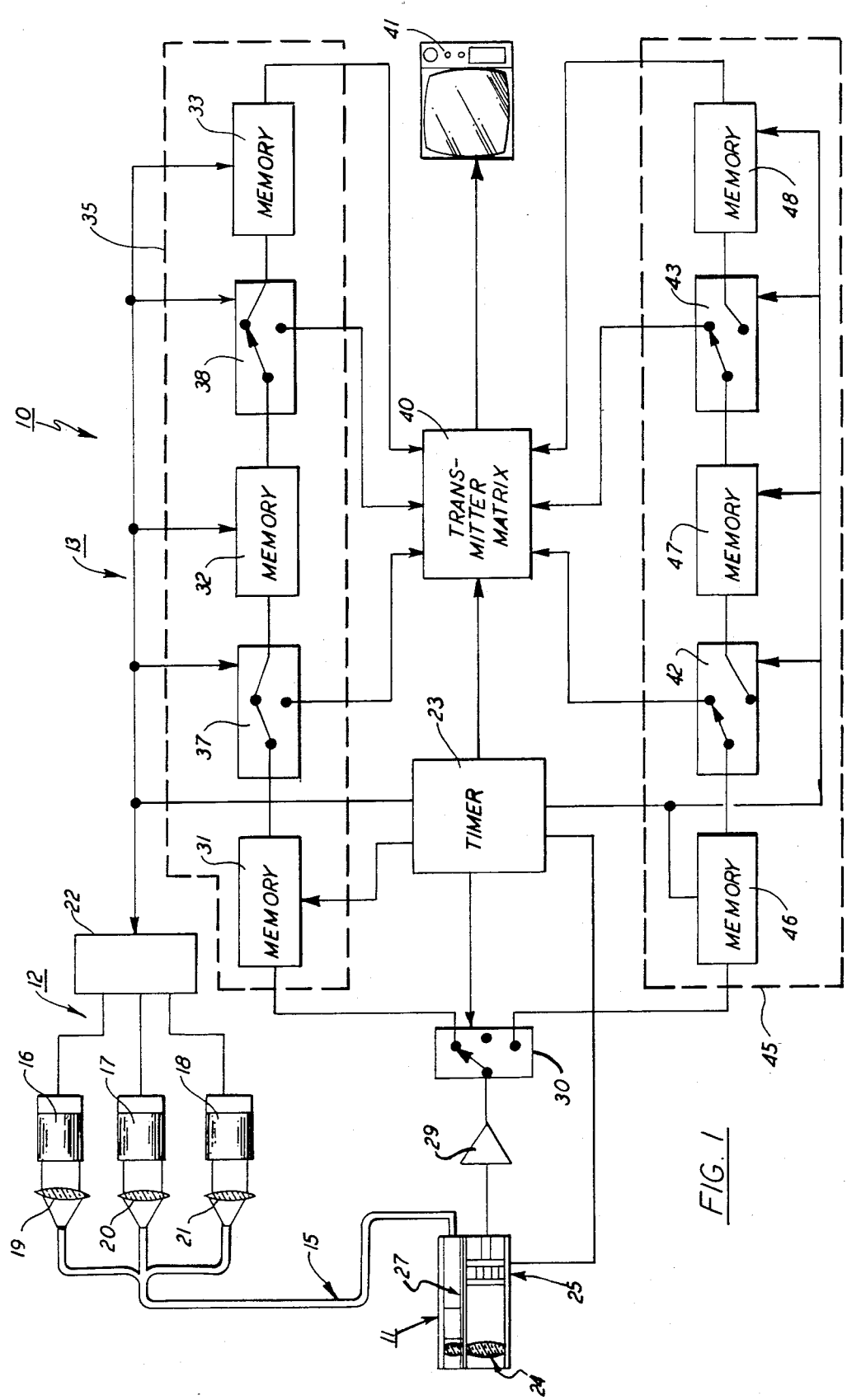
FIG. 1 is a block diagram illustrating an endoscope for providing a full color picture of a target which contains a compacted electro-optical package embodying the teachings of the present invention.

The present invention involves an electro-optical package suitable for use in either an endoscope or borescope that is capable of furnishing full color image data of a target situated within a generally inaccessible region which can be viewed on a television screen. As illustrated in FIG. 1, the apparatus embodying the invention will be described in greater detail in reference to an endoscope, generally designated 10, which includes a viewing head 11 that is connected to an external electrical section 13 by means of a hollow flexible sheath 14 (FIG. 2). An external illumination section 12 is also connected to the head by means of the sheath for illuminating the target. In assembly, the viewing head is mounted at the distal end of the sheath and is connected to both the illumination and electronics sections by suitable transmission lines which are passed through the sheath. The number of components required to furnish the image data are not only minimized but are also packaged in a compact housing to provide for the maximum utilization of space and ease of assembly. As a result, the size of the viewing head is greatly reduced thus enabling it to reach relatively confined regions with a minimum amount of risk and patient discomfort.

The external lighting system 12 contains three independent flash lamps 16–18 that function in association with suitable lens/filter units 19–21 to generate separate beams of red, green and blue light. Light from the lamps is directed into the light receiving or proximal end of a fiber bundle 15. The proximal end of the bundle is trifurcated with each arm of the trifurcation being positioned to receive illumination from one of the light sources. The firing sequence of the lamps is regulated by a control circuit 22 which triggers the lamps in response to a control signal from the master timer 23. The fiber bundle 15 passes into the viewing head through the sheath and is positioned in the head to direct light directly into the target region. The light exit or distal end 28 of the bundle is bifurcated to uniformly illuminate the target region and to minimize image shadowing.

An imager sensor housing, generally referenced 27, is also mounted within the viewing head of the instrument. The housing contains an optical lens system 24 that is arranged to focus a light image of the illuminated target upon the image recording surface of a solid state sensor 25 positioned within the image plane of the optics. In practice, the imager sensor is a charge coupled device (CCD) that is arranged to provide an electrical output signal that is indicative of the image data recorded thereon. As will be explained in greater detail below, output signals are passed via a transmission line through amplifier 29 and then on to the external electric section 13.

The lamps are arranged to be fired in an ordered sequence that is related to the field period of the video system. The target is illuminated with red, green and blue light to create color separated images of the target which are recorded by the image sensor. The recorded data is converted to an electrical signal that is fed out in a line by line sequence to electronic section 13. Data concerning each separated image is loaded initially into a first serial shift register 35 containing three memories 31-33. Data loading is achieved automatically by sequencing electronic switches 30, 37 and 38 in response to a signal from the master timer 23. At the start of a first odd field period, the stored data is delivered simultaneously into the transmitter matrix 40 which processes the color information and places it in a format that is compatible with either a NTSC system or a RGB monitoring system.

During the next occurring even field period, the noted electronic switches are automatically repositioned along with switches 42,43 contained in a second serial register 45 whereupon updated image information clocked out of the sensor is loaded into memories 46-48. Here again, at the end of the field period, the switches are recycled causing the updated data to be fed into the transmitter matrix. As can be seen, by relating the firing sequence of the lamps to the field period of the video system, a single image sensor can be utilized to feed a continuous stream of new color separated target information to the video processor.

With further reference to FIGS. 2-4, there is shown in greater detail the component parts of the viewing head 11. The head includes a tubular body 49 that is small enough to allow the head to be passed into relatively small openings to reach restricted areas that heretofore have been generally inaccessible to this type of instrument. One end of the body is fitted into the distal end of the flexible sheath 14 and is operatively connected to a steering mechanism 50 so that the head can be maneuvered to place the optics upon a desired target. An end cap 51 is threaded onto the opposite end of the body and is passed over both an O-ring seal 52 and the distal end of the sheath. The end cap is contoured to provide a smooth outer surface at the tip of the head and also prevents the sheath from being rolled back during the insertion and maneuvering of the head. The front face of the viewing head has an opening or window 53 that permits light to pass freely into and out of the housing. As noted, colored light transmitted by the fiber bundle 15 illuminates the target and provides color separated images thereof. Color separated images of the target are reflected back through the optics 24 and are focused in sequence upon the image recording surface of the sensor 25.

A hollow cylindrical image sensor housing 27 is mounted within the main body 49 of the viewing head 11 and contains the electro-optical components needed to provide target information. The optical elements of the lens system 24 are mounted in alignment with a lens barrel which, in turn, is partially threaded into the front of housing 27. An epoxy end seal 54 is applied over the front of the barrel to furnish a fluid tight seal between the housing and the first element 72 in the lens array. The seal prevents fluids and gasses from passing in and out of the front of the housing. The lens system is designed so that it has a relatively short back focal length thus minimizing the distance from the last optical element to the image plane 69 of the system. The image plane is disposed behind the lens barrel within the housing opening.

A circular or disc-like substrate 57 formed of alumina, or any other suitable non-conductive material, is fitted into the housing opening and is positioned behind the image plane in parallel alignment therewith. The solid state image sensor 25 is mounted upon the front surface of the substrate with the image recording surface of the sensor being supported in coplanar relationship with the image plane of the optics to permit color separated images of the target to be focused thereupon. An optically clear resin is cast upon the front surface of the substrate assembly to encapsulate the sensor element within a protective coating 67. The front face of the coating, in assembly, is seated against a radially disposed shoulder 68 formed in the housing opening to both locate the recording surface of the sensor in the desired image plane and to prevent the sensor assembly from shifting its position once it has been assembled.

Preferably the single chip image sensor is a charged coupled device (CCD) having a series of pixels arranged in rows and columns which are compatible with the format of video receiver 41 (FIG. 1). The image recording surface of the CCD may be rectangular or square in form as illustrated in FIG. 4 so that the sidewalls of the chip are bordered by four arcuate shaped access sections 59-59 on the support substrate. Preferably the diagonal distance between the corners of the CCD is about equal to the diameter of the substrate so that a minimum amount of space is utilized.

As best illustrated in FIG. 3, a hybrid circuit board 80 is also mounted within the cylindrical image sensor housing immediately behind the support substrate. The circuit board contains circuitry for supporting the operation of the image sensor and for processing signal information that is exchanged between the sensor and the external electrical section. In order to further conserve space, circuitry may be printed on both sides of the board. The circuitry is electrically connected to a series of conductive pins in a manner to be explained in greater detail below to provide the necessary communication between the various system components. The number of components supported on the board will vary in accordance with the service requirements of the CCD, the need for preamplification or filtering of the output signal and other related operations.

Referring now to FIGS. 2-4, transmission lines 81—81 are passed through the sheath which carries video and control signals into and out of the viewing head. Connections between the transmission line and the CCD and the sensor support circuits are made through means of relatively easy to assemble connector pins. A first set of pins, herein referred to as the sensor pins 75—75, are mounted in the CCD support substrate adjacent to the side walls of the sensor within the access areas 59—59. The pins are furnished with enlarged heads 77 having a height substantially equal to the thickness of the CCD so that the top surface of each pin is in coplanar alignment with the image recording surface of the sensor. Wire leads 73—73 are connected between the heads of the pins and the CCD terminals 73—73. In this particular embodiment of the invention, six pins are shown mounted in three access regions; however, the number and location of the pins may vary in accordance with the CCD configuration and electrical requirements of the system.

The length of the sensor pins may also vary. As shown in FIGS. 2 and 3, a first group of pins 75a having short shanks that pass through the CCD support substrate and terminate at the underlying circuit board. The short shank pins are employed to connect the CCD to the electrical circuitry mounted on the board. A second group of sensor pins 75b are each furnished with a longer shank that passes through both the substrate and the circuit board and which is electrically bonded directly to one of the transmission lines 81—81. The longer shank pins thus provide a direct connection between the CCD and the external electrical section.

Another set of pins, herein referred to as the circuit board pins 83—83, are passed through the circuit board and serve to connect board mounted components to the remaining transmission lines. The configuration of the second set of pins is similar to that of the sensor pins in that each contains an enlarged head 84 and an elongated shank 83 which passes through the board and is electrically bonded to one of the transmission lines to complete the electrical wiring within the housing. In practice, the circuit pins are passed through conductive runs such as run 86 shown in FIG. 3, that are printed on the board which places the pin in electrical communication with one of the electrical components such as a preamplifier 87.

The back of the sensor housing is closed and sealed using an elastomer block 88 of resin or other suitable material thereby hermetically sealing the electrical and optical components within the housing. A gas tight chamber 71 is thus established between the lens system and the image sensor which is filled with an inert gas, such as nitrogen, to prevent water from condensating on the system components and to further protect the components from harmful contaminants and the like. As should now be evident, by packaging the optic and image recording components in a superimposed relationship within a small housing, not only compacts the structure but also facilitates the mounting and assembling of the component parts contained within the viewing head. Furthermore, the entire compacted unit is hermetically closed and sealed thereby securing the components in assembly and protecting them from harm.

Figure 5:
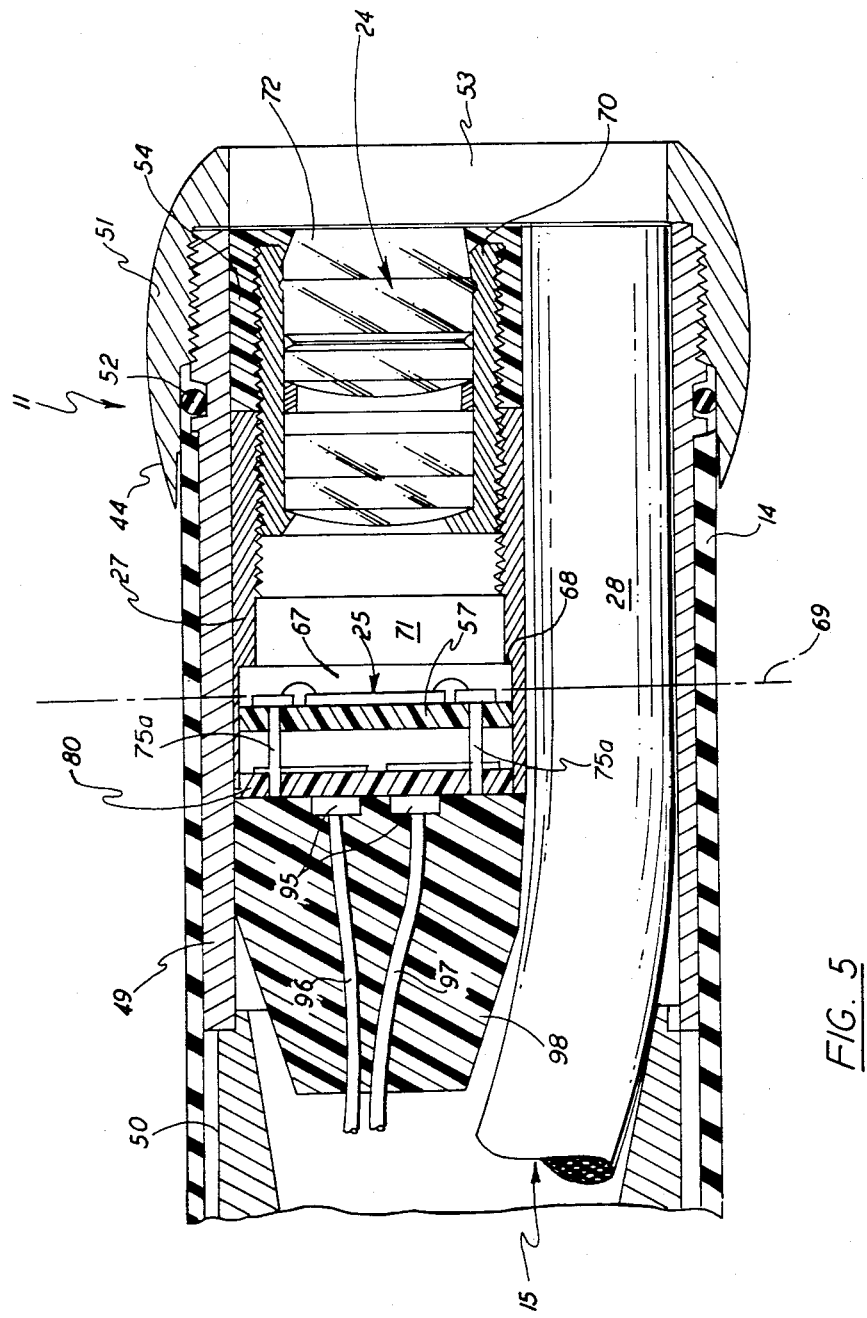
FIG. 5 is an enlarged side elevation in section of a viewing head suitable for use in an endoscope illustrating another embodiment of the invention.

As is typical in most endoscope or borescope applications, the length of the leads connecting the image sensor and the external electrical section is generally relatively long. As a consequence, transmitting signals into and out of the viewing head poses certain transmission problems. Although these problems might be alleviated by matching the imager impedance to the line impedance, or utilizing an impedance matching device such as an emitter follow in the circuitry, it may be more practical to couple the image sensor unit to the external electrical circuit by optical transmission lines. As illustrated in FIG. 5, the electrical transmission lines shown in FIG. 2 are replaced by an optical input line 96 and an optical output line 97 that are adapted to transmit optical signals between the two remote stations. A pair of transducers 95—95 are secured to the back surface of the circuit board which are coupled to the two transmission lines and the sensor circuitry. The transducers serve to convert the optical transmission signals to electrical signals or vice versa in a manner that is well known in the art. Accordingly, input and output signals to and from the image sensor can be transmitted over relatively long distances without the danger of cross talk or interference between the lines. Here again the substrate 57 and the circuit board 80 are mounted as explained above however, only the shorter pins 75a are required to electrically connect the two in assembly.

While this invention has been described with reference to the details as set forth above, it is not limited to the specific structure as disclosed and the invention is intended to cover any modifications or changes as may come within the scope of the following claims.

We claim:
1. A compact electo-optical imager assembly for use in the viewing head of an endoscope that includes:
an elongated housing having a circular opening passing axially therethrough and having a lens system mounted in the front of the opening for focusing an image of an external target onto an image plane situated inside the opening,
an imaging unit mounted in the opening behind the lens system having a substantially circular substrate for supporting a solid state rectangular image sensor in a position to record image data focused in said image plane and convert said image data to an electrical output signal, and a circuit board mounted behind the substrate having circuit means connected to the image sensor,
transmission lines passing into the housing through the back of the opening that are connected to the imaging unit for carrying signals into and out of the housing, and
sealing means for hermetically closing the housing.

2. The assembly of claim 1 that further includes connector pins passing between the disc and the circuit board, said pins having expanded heads seated on the front face of the disc adjacent to one or more side walls of the disc, and lead wires connecting the heads to the chip.

3. The assembly of claim 1 that further includes an optically clear coating for encapsulating the image sensor.

4. The assembly of claim 2 wherein a portion of the pins are passed through the circuit board and are connected to transmission lines and the remaining pins are connected to circuit means contained on the board.

5. A compact electo-optical imager assembly for use in the viewing head of an endoscope that includes:
an elongated housing having an opening passing axially therethrough and having a lens system mounted in the front of the opening for focusing an image of an external target onto an image plane situated in the opening,
an imaging unit mounted in the opening behind the lens system having a substrate for supporting a solid state image sensor in a position to record image data focused in said image plane and convert said image data to an electrical output signal, and a circuit board mounted behind the substrate having circuit means connected to the image sensor,
transmission lines passing into the housing through the back of the opening that are connected to the imaging unit for carrying signals into and out of the housing,
sealing means for hermitically closing the housing, and an inert gas contained within said sealed housing.

6. A compact electo-optical imager assembly for use in the viewing head of an endoscope that includes:
an elongated housing having an opening passing axially therethrough and having a lens system mounted in the front of the opening for focusing an image of an external target onto an image plane situated in the opening, an imaging unit mounted in the opening behind the lens system having a substrate for supporting a solid state image sensor in a position to record image data to an electrical output signal, and a circuit board mounted behind the substrate having circuit means connected to the image sensor, said circuit board containing circuit means on both sides thereof, transmission lines passing into the housing through the back of the opening that are connected to the imaging unit for carrying signals into and out of the housing, and sealing means for hermetically closing the housing.

7. A compact electo-optical imager assembly for use in the viewing head of an endoscope that includes:

an elongated housing having an opening passing axially therethrough and having a lens system mounted in the front of the opening for focusing an image of an external target onto an image plane situated in the opening, an imaging unit mounted in the opening behind the lens system having a substrate for supporting a solid state image sensor in a position to record image data focused in said image plane and convert said image data to an electrical output signal, and a circuit board mounted behind the substrate having circuit means connected to the image sensor, transmission lines passing into the housing through the back of the opening that are connected to the imaging unit for carrying signals into and out of the housing, sealing means for hermetically closing the housing, and transducer means mounted on the circuit board for converting input and output signals to the imaging unit to optical signals and said transmission lines carrying said optical signals to and from the transducer means.

* * * * *